United States Patent [19]

Carter

[11] Patent Number: 4,967,928
[45] Date of Patent: Nov. 6, 1990

[54] INVENTORY CONTROL INCLUDING INDIVIDUAL PATIENT LISTING AND MEDICAL CHART RECORD FOR MEDICATION CART

[76] Inventor: Cheryl L. Carter, 1306 Mayweather La., Richmond, Tex. 77469

[21] Appl. No.: 204,225

[22] Filed: Jun. 9, 1988

[51] Int. Cl.⁵ .............................................. G07F 11/00
[52] U.S. Cl. .............................................. 221/2; 221/3; 221/25; 221/69; 221/70; 221/92; 221/97; 221/124; 221/125; 221/154; 221/185
[58] Field of Search ..................... 221/3, 2, 9, 25, 69, 221/70, 71, 92, 97, 123, 124, 125, 126, 129, 130, 131, 154, 185

[56] References Cited

U.S. PATENT DOCUMENTS

| | | |
|---|---|---|
| 3,556,342 | 1/1971 | Guarr .............................. 221/154 X |
| 3,897,855 | 8/1975 | Patterson ........................ 221/70 X |
| 4,267,942 | 5/1981 | Wick, Jr. et al. ................ 221/92 X |
| 4,600,094 | 7/1986 | Hayashi et al. ................. 221/2 X |
| 4,635,053 | 1/1987 | Banks et al. .................... 221/2 X |
| 4,664,289 | 5/1987 | Shimizu et al. ................. 221/129 X |

FOREIGN PATENT DOCUMENTS 996077 6/1965 United Kingdom ................... 221/2

*Primary Examiner*—David H. Bollinger
*Attorney, Agent, or Firm*—Gunn, Lee & Miller

[57] ABSTRACT

A medicine cart is set forth and a means and method of dispensing medicines including narcotics on nurse rounds is disclosed. The cart includes a CPU with memory and various input devices. The cart has a locked section to secure narcotics. As nurse rounds are made, individual doses of narcotics and medicines or both are dispensed. At the end of the medication round, hard copies reflecting individual patient medications are printed, and beginning and ending narcotics inventories for the cart are also compiled. Chart entries for patients are likewise printed.

11 Claims, 3 Drawing Sheets

INVENTORY CONTROL INCLUDING INDIVIDUAL PATIENT LISTING AND MEDICAL CHART RECORD FOR MEDICATION CART

BACKGROUND OF THE DISCLOSURE

The present apparatus and method are directed to a means and procedure for dispensing medications as typically occurs in nurse rounds in a large hospital. In a typical situation, many patients, located in individual rooms, large wards or both, are deployed at or near a nurse station. Every morning and at other times during the day required nursing personnel begin medication rounds at which time a cart loaded with appropriate medications is pushed down the hallway from patient to patient (in rooms or wards) and individual medications are administered. Each round of the medication cart requires a rather complicated procedure. Individual orders for the various patients from a multitude of treating physicians must be examined and the cart loaded with the medications in advance. At the time of making the medication round, individual patient chart orders must be then reviewed at the cart so that prescribed medicine can be administered to each patient. A patient may receive more than one medication with each round, and the dispensing of such medications must be recorded with suitable verification to assure that the orders have been carried out. This typically involves multiple pieces of paper, one for the order from the treating physician, dispensing of that particular medication and written verification that it has been given to the patient. This is accomplished for every medication that is required, including those that are optional such as open orders where medication is prescribed on an "as needed" basis, meaning that the patient may or may not get that medication depending on their particular symptoms as dynamically determined. The foregoing is a tedious procedure and involves generation of substantial paperwork including written verification that the medications have been given which must be subsequently mounted in the patient's medical record. The nurse station normally collects individual medical records for each patient. The records can accumulate over a period of time, and, for someone who has been ill for some period of time, the record can become quite large. For people who have been hospitalized for weeks or months, their bound medical records can weigh many pounds.

The foregoing procedure is relatively complex, but an even more complex procedure is involved in the dispensing of narcotics. By definition, they are medications subject to prescription dispensing only. However, because they are viewed as inherently dangerous and are regulated by various Federal or State agencies, an extra sequence of steps is required in dispensing narcotics. The medical cart does not leave the floor. For medications other than narcotics an interchangeable rack of drawers is brought to the floor by pharmacy personnel. Narcotics are brought to the nursing station on the floor by specifically designated personnel. Prior narcotic inventory sheets with amount of drugs given in 24 hours and amount remaining are picked up by the pharmacy personnel once per day, usually at an early hour. The sheets are carried to the pharmacy to determine what stock to send by designated personnel who later deliver the narcotics and stock the cart. This person has responsibility for narcotics from the central pharmacy. The nurse accepts responsibility for the drugs when they arrive on the floor. In an alternate reloading process, the medication cart must be removed from the floor to be charged at the hospital pharmacy with its needed narcotics. At the pharmacy, the narcotics (in a locked vault or safe) are loaded onto the medicine cart. In turn, the medicine cart must be a locked vehicle where the narcotics are kept in a secure fashion. The narcotics are thus kept under lock and key arrangement where the key is checked out by a particular person who removes the cart after the cart has been loaded.

The cart must typically be charged with a specific number of narcotic medications. It is not uncommon to place 20-30 different types of narcotics in a cart, and the number of doses for each particular narcotic can be as high as 50. The cart is thus loaded with the requisite number of doses of the various narcotics and an inventory is then established. The inventory at the time the cart is loaded with narcotics is compared with the ending inventory minus the deletions which are administered to the various patients during nurse rounds. This added layer of paperwork creates significant delays in administering the medicines and narcotics. In addition, however, each patient receiving narcotics is provided with a written record at the time of dispensing so that the written record can later be incorporated in the patient's chart. Again, this represents the generation of an additional document which must be removed from the cart and integrated into the chart for that particular patient. On a large hospital floor with substantial patient census, the stacks of paperwork accumulated after a round of dispensing medications (including narcotics) is voluminous. It requires detailed record keeping at each step of the way. All of this clerical work basically detracts from quality attention to the patients; the nursing personnel must pay more attention to keeping the paperwork than to the patients. These are also problems with the human recorder, errors require time to resolve or remain unresolved.

The present invention is a method and apparatus for overcoming these problems. It defines a medication cart which is equipped with an onboard computer system having suitable input devices such as a card reader, keyboard, and bar reader. The cabinet of the cart is divided into two portions, one being a conventional cabinet and the other portion constructed for enclosing narcotics. That portion is closed with a locked door, and includes means for dispensing narcotics only when prompted. The narcotics dispensing means has the improved form of a type of vending machine which delivers an order from the supply while storing the supply safely in the cabinet. Particular details of the present apparatus should be noted. Narcotics are stored in a locked cabinet. A large door covers over the locked cabinet. In addition, individual narcotics can be locked in individual compartments with their separate lock and key arrangement for each individual type of narcotic medication. It is not uncommon to load as many as 40 different types of narcotic medications onto a cart, each being provided with one or more units of dosage. For more popular narcotics, the total dosage may be perhaps 50 individual doses. For such popular narcotics, one approach is to load individual carpules into a holder and dispense single units so that the carpules slide out through a slot, administered in the fashion of a vending machine. The narcotic dispensing mechanism cooperates with the packaged form of narcotics, i.e. carpule or individual packets comprising a support card with a bubble or blister pack over an individual pill, tablet or capsule, and they are dispensed from the recesses of cabinetry so that only one dose is exposed at an interval.

Beginning and ending narcotics inventory is much more readily accomplished. For instance, narcotics which are stored within the cabinetry and which are dispensed one unit at a time are never exposed. If 20 units were initially loaded, the number actually dispensed is measured in memory and the ending inventory for that particular medication is then calculated. Furthermore, the apparatus sustains an inventory at all points of dispensing along the nurse rounds. When the round has only been partly finished, a precise count is known even then so that inventory aboard the cart can be measured. In sum, narcotics inventory is obtained at all times, from the beginning inventory stored in the cart, to the last inventory. Moreover, painstaking hand counts or verification thereof can be avoided. The present invention is, therefore an apparatus implementing a method of operation whereby nurse rounds for dispensing medication (and especially including narcotics) are expedited. This is accomplished by providing a CRT or alternatively a printer on the cart which provides a continuing output of patient medications in a particular sequence. The sequence can be organized so that rounds proceed in the best sequence, beginning perhaps with the closest patient room to the nurse station and ending at the farthest or in some other sequence so that travel of the cart is orderly, and where each stop adjacent a patient is sequential and the medications are prompted to the nursing personnel in sequence. This is achieved by collecting all the medication orders, inputting the orders, sorting the orders into that sequence, collecting inventory to conform with the orders, loading the cart with that inventory and then arranging the patients medications in a particular queue. All medications including narcotics can then be drawn from the cart and administered quicklY. Moreover, as each medication is administered the personnel in charge of medication can provide verification back to the cart mounted CPU and ultimately obtain printed verification. This document is available by patient for incorporation in the patient chart typically maintained at the nurse's station. Dispensing errors could be reduced decreasing possibility of patients overdosage and potential associated litigation. Another problem that could be reduced is last medication charges; medication given and not charted are an expense that must be absorbed by institutions.

The apparatus includes a wheel mounted cart with a number of cubicles for storing medication. It includes a locked door which is released only by inputting appropriate codes. Behind the door, various narcotics are stored. Several narcotics are stored in individual cubicles or alternatively, different types of dispensing mechanisms operating in the fashion of coin operated vending machines deliver the various narcotics. Thus, the narcotics can be locked behind a first door and individual narcotics can be locked again, the looks being opened or the narcotics dispensed in individual dosage by means of coded inputs. After a medicine has been removed from the cart, it is packaged in an individual package where a bar code reader (in the form of a wand) is used to read the code to make verification that the dispensed medicine removed from the cart is in fact the medicine specified in the order. For narcotics, it is desirable to provide an extra step, namely identification of the nursing personnel and for this purpose, a keyboard or card reader or both is used. Personnel are normally provided with a badge which can be read by the card reader; in the event the badge is lost, protection can be obtained by inputting a personal identification number (PIN hereafter). Cart theft and pilferage is prevented by incorporating an alarm system and a battery monitor which provides alarm signals to personnel.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
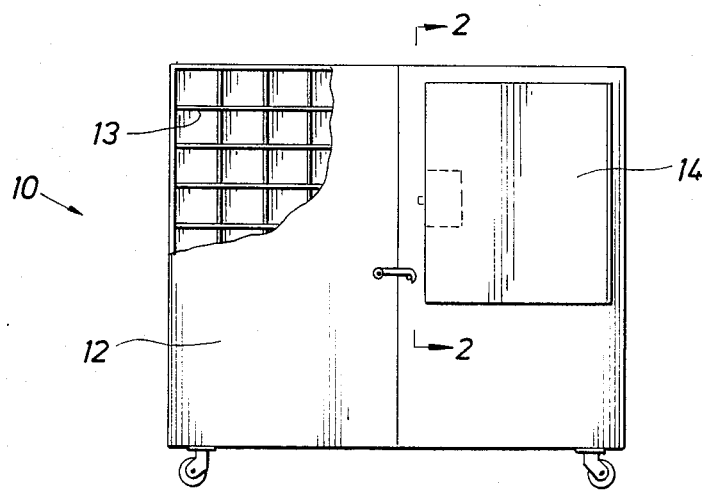
FIG. 1 is a side view of a medicine cart for use in nurse rounds with a portion broken away to show a set of internal medicine containers and further including a locked door over the narcotics stored in the cart.

Attention is directed to FIG. 1 of the drawings where a medicine cart for use in a hospital is illustrated. The cart 10 is supported on a set of wheels 11 and has a door 12 which closes over a number of cubicles for storage of medicine. Several cubicles are identified at 13. There are many cubicles so that the cart can be loaded with the various medicines from the hospital pharmacy. The medicines in the cubicles 13 do not include narcotics and will be described hereinafter simply with the notations "medicines" this being defined as those medicines which are administered from the hospital pharmacy and for which entries are ordinarily made on the chart of the patient. The cart is a large rectangular framework of sufficient size to hold an adequate number of medicines for a complete round. It is not uncommon to use the cart on two or three rounds during the day, typically the first round occurring in the morning for dispensing medicines to patients after breakfast. The same cart will be used for a second trip just after the noon meal, etc. Reloading of the cart may occur once per day, or more often if needed. Those medicines without narcotics are thus located in the cubicles 13.

Figure 2:
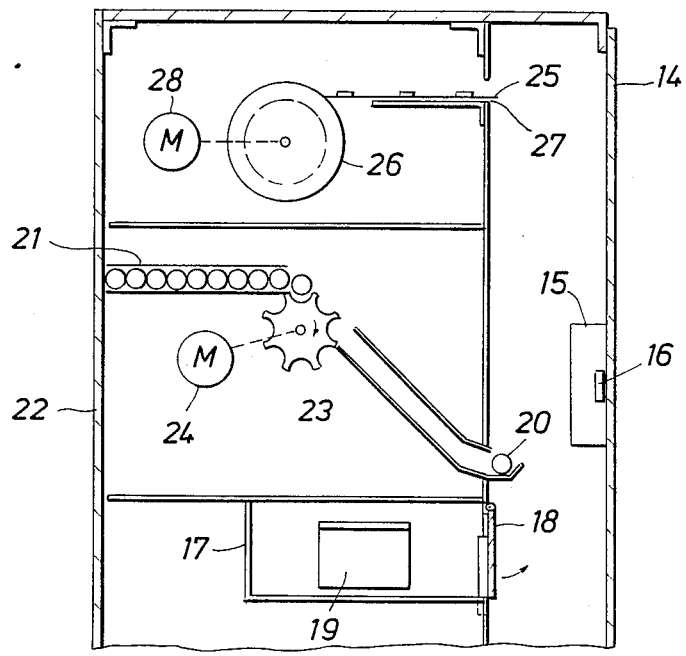
FIG. 2 is a sectional view along the line of 2—2 of FIG. 1 showing the locked narcotics portion and in particular showing individual narcotic dosage dispensing mechanisms which are operated on prompting from control circuitry and which dispense individual servings of narcotics.

The cart includes a locked door 14 which is mounted on a hinge and which covers storage containers or cubicles for the narcotics in the cart. The term narcotics refers to any medication which includes narcotics and which must ordinarily be handled in locked storage cabinetry, vaults, etc. all in accordance with the appropriate state or federal regulations for handling such narcotics. All types or grades of narcotics on board are collectively grouped in this term, the narcotics being stored behind the locked door 14 and typically stored in individual packages, carpules, individual dose blister packs, etc. More will be noted concerning this hereinafter. As shown in FIG. 2 of the drawings, the door 14 has a lock 15 on the interior, and the lock has a protruding hasp 16 which is shown in dotted line in FIG. 1. The door is locked, and can not be opened with a key, rather it is opened only with inputting a particular code at a keyboard or through the use of a card reader as will be described. When the proper signal has been input by the proper personnel, then the door 14 is unlocked and rotates on its hinge to permit access to the various narcotics stored in the containers or cubicles behind the door 14.

FIG. 2 shows individual narcotics dispensing mechanisms. A single cubicle 17 having its own assigned locked door 18 is shown in FIG. 2. An individual dosage in some suitable form is identified at 19 and is received in the cubicle 17. This approach isolates the individual narcotic 19 so that a second locked door must be opened to get access to it.

For convenience, especially in administering those narcotics which are used in quantity such as injectable morphine for pain reduction vending machines are included which deliver such individual doses. Several individual morphine carpules 20 are identified at 20. They are stored in a magazine 21 which is deep within the recesses of the cart. The magazine 21 is not accessible through the door 14. Rather, it is loaded through a back door 22 which is locked at the hospital pharmacy. A dispensing mechanism 23 dispenses single carpules of this particular narcotic. The dispensing mechanism is operated by a drive means such as a motor or stepping motor 24. The motor is connected so that the dispensing mechanism drops the single carpule out of the closed and sealed storage area and positions it where nursing personnel can quickly remove the carpule for subsequent use. The carpules are dispensed upon providing proper instructions to the control circuitry and computer which will be described in FIG. 3.

Other types of narcotics, typically having the form of pills, capsules or tablets are delivered in the form of a blister pack on a card. A single dosage is typically mounted on a card by means of a bubble or blister pack. The card is of specified rectangular dimensions and is joined to an adjacent card with a set of perforations. Several such cards are spooled on a drum 26, the individual cards 25 being serially connected. They extend through a narrow slot at 27 and can be torn from the spool one dose at a time. The spool is rotated by means of a drive motor 28 which again is operated by the control circuitry shown in FIG. 3. Thus, the motors 24 and 28 are periodically operated and each will dispense a single dose for each operation. This enables the card 25 to be pulled from the dispensing slot, or the carpule 20 to be removed by nursing personnel. The sequence in which the dispensed narcotics doses are used will be described in detail hereinafter.

Figure 3:
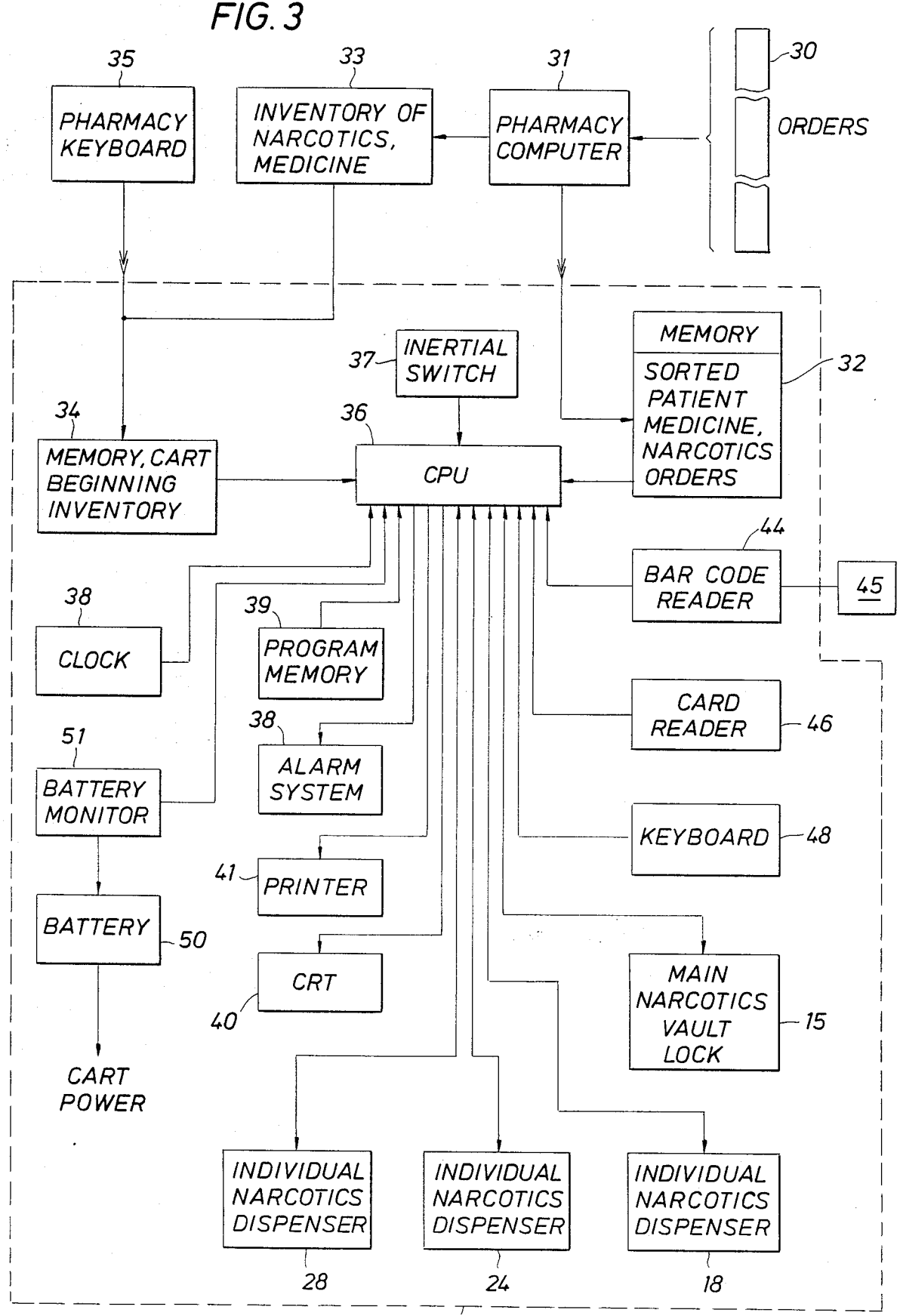
FIG. 3 is a schematic block diagram of the cart mounted control circuitry including computer with input and output devices for prompting medicine and narcotic dispensing.

Going now to FIG. 3 of the drawings, the computer system aboard the cart is illustrated and is located within the dotted line. Certain equipment located outside the dotted line will be described first because it relates to the procedure for obtaining various prescription medications including narcotics. Briefly, as illustrated in FIG. 3, for all patients which are located contiguous to a nurse station, whether in wards, private or semiprivate rooms, the various treating physicians write medical orders which include prescription requirements. The orders are collected. This is indicated generally at 30. The several orders for the various patients are collected and input to a pharmacy computer 31. The pharmacy computer reads the orders, converts the orders into a listing where the patients are sorted in a particular sequence. That sequence conforms to the travel route for the medicine cart 10. This may be in room order sequence, or any other sequence as appropriate; whatever the choice, the particular sequence is derived from the various orders for those patients and are then listed in that sequence. The sequential medicine orders are then transferred to a memory 32 on the cart which lists the patients by name in the desired sequence and also lists the medicine and narcotic orders. That is, the particular medications including narcotics are listed by patient name, room number, patient number as appropriate, particular medication, and size or dosage and other specific instructions necessary for the patients. That is stored in memory at 32. The pharmacy computer 31 also prepares an inventory of required narcotics and medicines indicated at 33. The inventory 33 is output for the pharmacist. In addition, it is input to the cart memory 34 which represents the beginning inventory of medicine including narcotics aboard the cart. Thus, the pharmacist is provided with the hard copy of the inventory and the inventory required for the cart is likewise located in memory. This provides suitable directions and instructions to personnel at the pharmacy for loading the cart. Conveniently, a pharmacy keyboard 35 is likewise included to enable input of the supervening instructions into memory so that changes in the medications loaded onto the cart can be recorded. For instance, the orders may specify a particular set of medications, but the pharmacist may know from experience that certain medications dispensed on a PRN basis should also be loaded into the cart. These additional inventory entries are made as the cart is loaded prior to return of the cart to the nurse station. The pharmacy has a precise list of medications loaded onto the cart (for billing and inventory purposes) and the cart itself is provided with the memory 34 with an accurate list of the medications including narcotics aboard the cart.

At this point, the cart can then be removed from the pharmacy to the nurse station preparatory to the first round of the day, typically just after breakfast. The cart at this point is equipped with a sorted patient list with all medicine and narcotic orders on the list, this being identified at the memory 32. The memory 34 is a separate cart inventory, the beginning inventory of all medications aboard the cart. This inventory will be decremented as deliveries are made out of the cart in the procedure described below.

Other details of the cart computer system should be noted. A CPU 36 is included. An inertial switch 37 is incorporated to indicate when the cart is moving. There are times when the cart is stationary, and indeed, movement may be totally undesirable. The inertial switch is useful with an alarm system 38 to indicate that the cart is being moved at the wrong moment. This can be incorporated to serve as a safety or theft alarm to prevent untimely movement of the cart. The alarm is switched on by the inertial switch should the cart be moved at the wrong time. However, the cart is intended for movement, and suitable operator encoding can be provided to permit the operator to override the inertial switch so long as the cart is under the personal control and jurisdiction of the proper nursing personnel. A clock 38 is likewise included and provides timing signals for the CPU. The cart also includes a program memory 39, it being understood that separate memories have been indicated at 32, 34 and 39 where in common application a single memory device will be used with separate memory fields. The system utilizes a CRT 40 to provide visible output prompts for the operator. Alternatively, a printer 41 can be used as an output device. Many of the transactions described below require a hard copy record and to this end, a printer 41 is preferably included. The printer, however, can be located remote from the cart and the cart connected with the printer temporarily after dispensing medications to the several patients whereupon the printer 41 is connected to the CPU by means of a convenient plug and socket to form the necessary hard copies to be placed in patient charts.

Several input devices are connected to the CPU. One is a bar code reader 44, another is a card reader 46, and another is the keyboard 48. The medications are preferably dispensed as individual doses, wrapped in protective film typically mounted on the card 25 as previously illustrated. The card is preferably printed with bar code identification so that the wand 45 can be used to read the bar code. Alternatively, a magnetic strip in a card is read by the card reader 46. This is the same device which is used for reading magnetic strips in credit cards or badges used for controlled access to factories and the like. The nursing personnel preferably use a card reader so that personnel identification is accomplished easily. The alternate third input is the keyboard 48 which can either be an alphanumeric keyboard, or can be provided only with numeric data. As will be explained hereinafter, certain instructions are input (the PIN number) so that security for the narcotics is assured and suitable documentation is generated while the person actually dispensing the medications is identified in conformance with regulatory statutes.

FIG. 3 further discloses an operator for the main narcotic vault lock 15. It is preferably electrically operated so that the hasp 16 is retracted when prompted by the CPU 36. A similar electrical signal is provided from the CPU 36 to open the lock 18 illustrated in FIG. 2. FIG. 2 also shows electrically powered motors 24 and 28 which function in individual narcotic dispensers. The system also includes a battery 50 periodically tested by a monitor 51 to provide indications of battery discharge. The battery 50 provides all the power necessary for operation of the equipment. Operation of certain of the equipment should be noted. The cart is equipped with a suitable mating plug and socket combination connected with an RS 232 terminal for inputting data. Data is input into the memories 32 and 34 through conventional techniques believed well known in the art. Data is additionally input through the bar code reader 44 by moving the wand 45 over medication packages to read the bars. As mentioned earlier, the packages can come in the form of flat cards with bars printed thereon. An alternative is bar markings on carpules, other containers, bottles, disposable pouches, etc. The card reader 46 normally reads a card which is pushed through a slot to form an input employee identification number or alternatively, identification of a particular dose affixed to the card. The keyboard 48 is a third optional input mechanism for receiving coded symbols representative of doses and particular medicines. The operator of the cart receives data including instructions and prompts by means of the CRT 40 or the printer 41. In response to these, the operator performs the next step in delivery of the medications to the various patients under charge of the particular operator.

Figure 4:
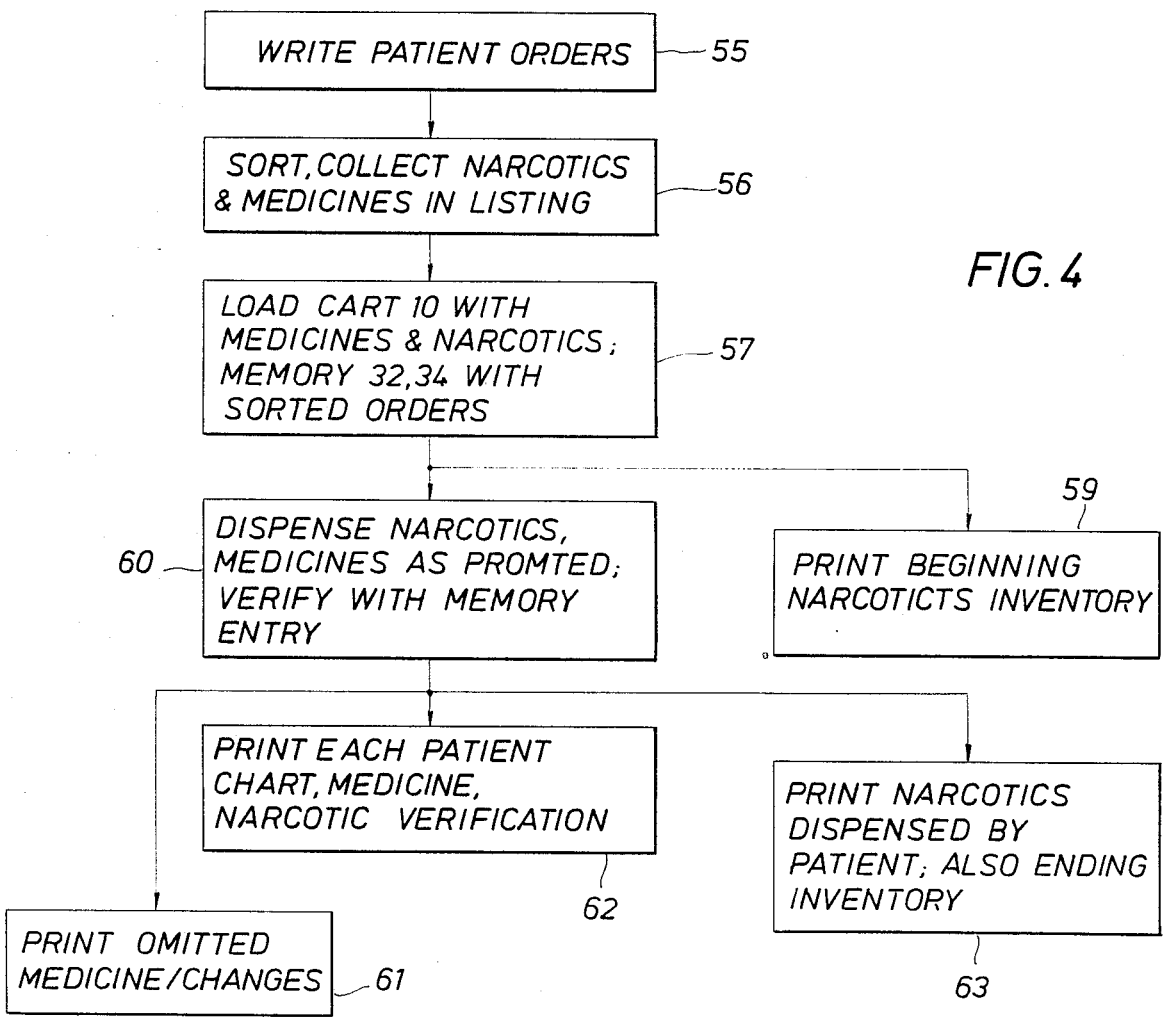
FIG. 4 is a flow chart of activities relating to order preparation, medicine and narcotic loading into the cart, and dispensing during operation.

FIG. 4 of the drawings is a flow chart listing certain steps that must be undertaken and begins with the first step 55 of writing patient orders. This is normally carried out by the treating physicians. These orders are then collected and input for sorting, and from the orders, the collected narcotics and medicines are then grouped as a listing 56. This step is involved in the data generated for the memory 32. This step typically involves identification of the patients by name and room or bed location, patient number according to the hospital records, date and time, particular medications including narcotics and the doses required for such medications. In addition, the treating physician is identified. This list, after sorting, can be conveniently converted into a collective inventory as exemplified at 33 in FIG. 3. In any event, the next step is to load the cart 10 with the various medicines and narcotics. It is physically loaded by placing the various medicine containers in cubicles in the cart 10. Simultaneously, the memory 34 is loaded with the beginning inventory. Simultaneously, the sorted patient orders at 32 are loaded into memory. At this juncture, the cart is normally removed from the pharmacy under control of proper personnel. In fact, cart movement can be defeated by the alarm system which sounds an alarm if the cart is moved by unauthorized personnel. Movement by the proper personnel requires inputting personnel identification through the card reader 46 and keyboard input of the PIN number. This is stored so that the memory knows what particular person removed the cart along with the various medicines and narcotics on the cart.

After the cart has been loaded, the next step is to print out a beginning narcotic inventory as shown at 59. If desired, this can be verified with a hand-count as the cart is removed from the pharmacy. Perhaps, one sequence is to compile a list of the narcotics necessary for the cart, draw the narcotics from the supply in the vault at the pharmacy, load the cart with such narcotics, and then utilize the beginning narcotics inventory from the step 59 to assure that proper counting has occurred. Counting need not be difficult. For instance, the cards 25 shown in FIG. 2 are numerically labeled. This avoids the need to count all the cards, rather, the cards are supplied on a spool so that the last card showing provides the number of cards. It is not uncommon to load between 20 and 40 cards, the cards being serially connected at tear-away perforations so that card verification is quickly accomplished.

The next step shown in FIG. 4 is the step 60 of dispensing the medicines and narcotics as required. Step 60 is carried out by moving the cart from bed to bed or for all the patients under the responsibility of the particular nurse administering the medications and narcotics. As mentioned earlier, this typically starts when the nurse moves the cart from the nurse's station to the first patient's location. The patients are listed in memory in this sequence. That is, the memory preferably stores the patients in a sequence which is convenient and easy for the nurse. The medicine cart is thus transferred from the pharmacy back to the nurse station and the round can begin immediately so that the first patient is immediately prompted for the nurse. Such prompts can be output either through the CRT or the printer. As medicine is delivered to the patient, the delivery beginning with removal from the cart, the instructions for that particular dose can be prompted to the nurse and the nurse can thereafter perform a verification input.

Consider an easy example. Assume that the first patient is prompted on the screen and only a single medication need be administered. That particular medication is prompted onto the screen, and the nurse then draws that particular medication from the cart in the indicated dosage. Assume that the particular medication is supplied in card form where the pill, tablet or capsule is in the blister or bubble pack. The card has a bar code identification number. The wand 45 is passed over the bar code. This indicates to the computer that the particular card has been withdrawn from inventory on the cart. Thus, the nurse is able to read visually on the card the particular medicine removed from the cart. Verification is bolstered by the bar code reading step which matches the bar code on the card with the instructions prompting the nurse. This interlocking approach assures proper verification. Once the medicine has been verified, the nurse can then leave the cart, step to the bed of the patient (typically only a few feet away), give the medicine to the patient, and then return to the cart. A suitable entry (such as PIN number) is then performed by the nurse to indicate that that transaction has been completed, meaning that the right medicine from the order has been dispensed from the cart, verified, administered to the patient, then reverified as having been delivered to the patient in the prescribed manner. This step 60 thus assures quality medical care to the patient in that confusion as to medication, misreading of labels and other mishaps in medication do not occur. The foregoing procedure is used both for narcotics and medicines. To remove narcotics from the cart, additional steps are required. This will be discussed with FIG. 5.

As the nurse makes the patient rounds, certain exceptions may arise. TYpical exceptions are discharge of a patient so that no medication is administered. Another exception may occur where the patient has been removed from that particular bed or room and transferred to another health care facility, for an example, an intensive care unit (ICU). There may be discretion for the nurse in administering some drugs such as PRN instructions, and in that event, it may be necessary for the nurse to verify back to the computer that such exceptions were implemented. The step 60 contemplates transfer back into the equipment of the exception events. In a typical medicine round where 50 patients are attended, it is not uncommon for five or ten changes or alterations to occur.

After the cart has traversed the patient area and has been returned to the nurse station, the step 61 is operated so that all the changes or omitted medications are listed. The step 61 serves primarily as a limited set of corrections to be implemented into various medical charts. It is important, however, that every medical chart receive a hard copy entry verifying that the orders were actually administered, and to this end, the step 62 describes printing of each patient's chart entry. This is the step of printing a hard copy for each patient which reflects the actual medication administered including all the support data such as particular medication identification, dosage and amount, the time at which the medicine was administered, name of the treating physician, name of the nurse personnel who administered the medicine and any other data which might be necessary. It may be appropriate for the nurse to input data in a variety of circumstances accomplished through the use of the keyboard, and which is stored momentarily until hard copy is made. If 50 patients were involved in the rounds, this step would typically print 50 separate pages so that each page can be placed in the respective patient charts. The entries on the various chart pages can be as simple or as complex as they have been when prepared by hand.

The step 63 relates to inventory of the narcotics. Part of this is to print the total narcotics transactions during the rounds, that is, to list all the narcotics prescribed and administered to the patients on the round. This represents removal of narcotics from cart inventory, and after that is done, the ending inventory is prepared. As desired, it can be verified by actual count. Counting, however, is made much easier by the spooled cards which can be visually counted simply by looking at the last card. If the spooled cards initially counted to card 40, and the number showing is 25, then 15 units were dispensed, and 25 remain on the spool or on inventory.

Beginning with the inventory loaded on the cart and with the decremented entries for the various patients, hospital costing to the chart can also be readily accomplished so that total charges are compiled easily.

Nurse Activity

Figure 5:
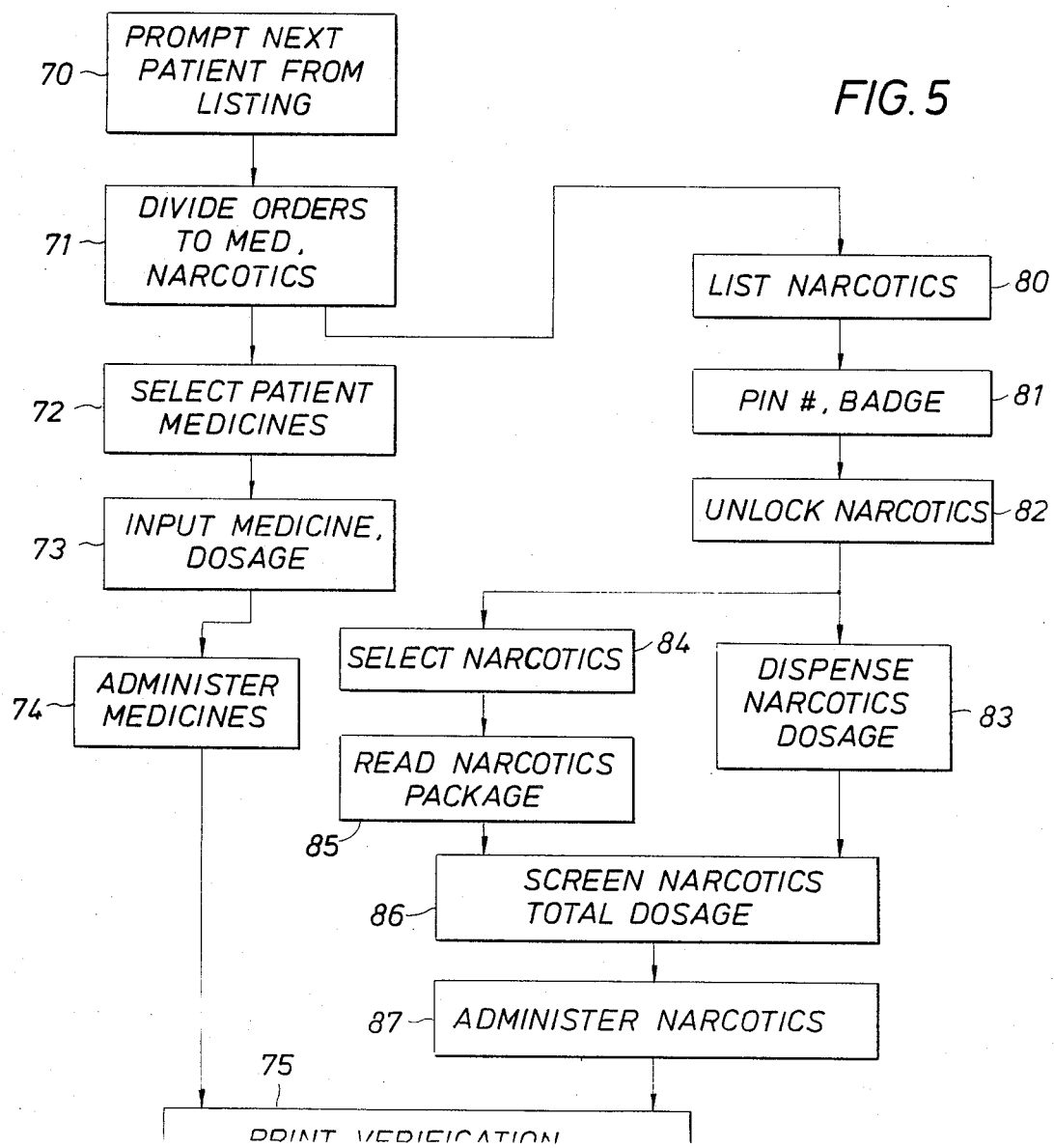
FIG. 5 is a flow chart of actions undertaken by nursing personnel to dispense medicines and narcotics during rounds.

Going now to FIG. 5 of the drawings, the routine which involves the nursing personnel is illustrated. This assumes that the loaded cart equipped with all the necessary medicines and narcotics and having the memories 32 and 34 is pushed to the immediate vicinity of the nurse station.

FIG. 5 shows the sequence of operations after the cart 10 has been moved from the station to the first patient bed. The first step is identified at 70 where the nurse prompts the computer to list the first or next patient. This step 70 proceeds immediately to the next step 71 which divides the order into two groups, namely medicines and narcotics. The division of the patient orders into medicine and narcotic grouping enables the nurse to proceed immediately to the next step of selecting the particular patient medicines at step 72. This requires the nurse to draw a particular dosage from a storage cubicle. This is indicated by the nurse back to the equipment by inputting the type of medicine and dosage, see step 73. Step 73 can be implemented bY using the bar code reader, and keyboarding the dosage as an example. Alternatively, if the medication is delivered from the cart in the form of individual cards, they can be quickly verified and dosage is obtained. The next step for the nurse is to administer the particular medicines to the patient at step 74. If no narcotics are required, the last step involved for that particular patient is to obtain a printed verification at the step 75. This is actuality the printed hard copy verification shown at step 62 in FIG. 4.

In the description above, it was assumed that no narcotics were included. Rather, assume now that narcotics are included in the particular treatment regime for that particular patient. In that event, the medicines may be obtained as described through the step 73. Then, the nurse next proceeds with the alternative subroutine beginning with the step 80 which requires prompting the screen with the listed narcotics necessary for that particular patient The next step 81 for the nurse is to input a badge and PIN number. At this juncture, the door 14 is unlocked, this being accomplished at step 82. If the narcotic is stored in one of the special dispensing mechanisms shown in FIG. 2, the next step is to operate that equipment at step 83 which dispenses either the carpule 20 or the card 25. Alternatively, the narcotics may be in individual cubicles behind the vault door 14. If that is the case, the nurse then by hand selects the narcotics shown at the step 84. In this instance, the package is then read. This may be accomplished with the wand which reads the bar code numbers. Alternatively, it can be read visually by the nurse and the code number from the package is then input through the keyboard at the step 85. This data includes specific identification of the narcotics by a code number and quantity or dosage. Whether it proceeds to the step 83 or the alternate step 85, the particular narcotic by code number and the particular dosage removed is then flashed on the screen which shows the total dosage of all narcotics, this being step 86. The next step is for the nurse to administer the narcotics in the conventional and intended fashion, see step 87. This step can be accomplished simultaneously with the step 74 previously mentioned. At the conclusion of administering the narcotics, the printed verification is then obtained at step 75 which in this instance will include the narcotics which were administered. After the nurse finishes with that particular patient or at that ward or hospital room, the nurse then moves the cart to the next patient bed and prompts the system to show the next patient, hence returning to step 70 for repetition of the cycle.

Going back now to FIG. 4, it will be observed that the nurse at the conclusion of the medication round then has the cart which has been partially depleted of supplies, a printed list of omitted medicines or changes from step 61, printed beginning and ending narcotics inventory (see steps 59 and 63) and can also obtain written drug verification for each patient as indicated at the step 62. If there were N patients, a page is printed for each patient, and the N pages can then be detached from one another and incorporated in the various patient charts. Indeed, a page can be obtained even if no medications were administered to the patient on that round.

This materially speeds up the medication round by the nurse. It has the further benefit of quickly providing the proper paperwork so that the patient charts are documented, and the narcotics (beginning and ending) inventories are printed all the necessary entries are included such as the particular medications or narcotics, dosage, patient name, room number and patient identification number, prescribing physical identification and the nurse who administers the medications. The cart at this time can be returned to the nurse station, closed and locked. If it is accidentally moved, an alarm will be sounded. If is necessary to return the cart to the pharmacy, the cart can then be pushed to the pharmacy after the alarm has been disarmed by properly inputting personnel identification such as through the card reader and a PIN number. The data output from the cart can be in the form of a written hard copy assuming a printer is placed on the cart. Alternatively, it can collect all the data, record the data in some magnetic medium such as a floppy disc, thereby permitting the floppy to be transferred to a small computer at a convenient location which is then operated to print out the various hard copy documents just described. Moreover, all the safety and security regulations required for the handling of narcotics are followed in this procedure. One desirable feature is modular construction in which the electronic components on the cart are contained in a removable chassis for removal and service work. It might also be desirable to issue a key for conventional key locking of the lock shown in FIG. 1. This key override feature must be safeguarded by proper key retention, for instance, at the pharmacy. In the untimely failure of the computer controlled lock, the key can be used as an override.

While the foregoing is directed to the preferred embodiment, the scope is determined by the claims which follow.

What is claimed is:

1. A medication cart for dispensing narcotics to a plurality of patients during nurse rounds, the cart comprising:

(a) a portable cart having N compartments for narcotics stored in said compartments wherein said N compartments are covered by a locked cover over said compartments and said cover comprises a hinged door fastened with a lock means and wherein said door extends over N individual narcotics compartments sized for receiving individual narcotics therein in specified dosage;

(b) counter means for counting doses of narcotics in each of said N compartments, said counter means having input means thereto for receiving an entry representing the initial doses of narcotics in each of said compartments, said counter means decrementing the beginning narcotics count as doses of narcotics are removed from individual compartments to form an ending narcotics count of narcotics in each of compartments of said portable cart after the cart has moved among a plurality of patients; and (c) a second door means with lock thereon for locking an individual narcotic in an individual compartment in addition to said door.

2. A medication cart for dispensing narcotics to a plurality of patients during nurse rounds, the cart comprising:

(a) a portable cart having N compartments for narcotics stored in said compartments;

(b) lock means for securing said compartments having narcotics therein;

(c) counter means for counting doses of narcotics in each of said N compartments, said counter means having input means thereto for receiving an entry representing the initial doses of narcotics in each of said compartments, said counter means decrementing the beginning narcotics count as doses of narcotics are removed from individual said compartments to form an ending narcotics count of narcotics in each of said compartments of said portable cart after the cart has moved among a plurality of patients; and (d) a plurality of attached identical cards, each of said cards storing a selected does of a narcotic and including means for serially dispensing such narcotics in card form.

3. The apparatus of claim 2 wherein said cards are stored in said compartments within said cart and said cards are dispensed through a slot in said compartment.

4. A medication cart for dispensing narcotics to a plurality of patients during nurse rounds, the cart comprising:

(a) a portable cart having N compartments for narcotics stored in said compartments;

(b) lock means for securing said compartments having narcotics therein;

(c) counter means for counting doses of narcotics in each of said N compartments, said counter means having input means thereto for receiving an entry representing the initial doses of narcotics in each of said compartments, said counter means decrementing the beginning narcotics count as doses of narcotics are removed from individual said compartments to form an ending narcotics count of narcotics in each of said compartments of said portable cart after the crt has moved among a plurality of patients; and (d) a first means for indicating movement of said cart to a CPU which then activates an alarm system wherein said first means includes second means defeating said alarm system so that movement of said cart is accompanied by sounding of said alarm system subject to override.

5. The apparatus of claim 4 further including operator controlled input means for defeating operation of said alarm system.

6. A medication cart for dispensing narcotics to a plurality of patients during nurse rounds, the cart comprising:

(a) a portable cart having N compartments for narcotics stored in said compartments;

(b) lock means for securing said compartments having narcotics therein;

(c) counter means for counting doses of narcotics in each of said N compartments, said counter means having input means thereto for receiving an entry representing the initial doses of narcotics in each of said compartments, said counter means decrementing the beginning narcotics count as doses of narcotics are removed from individual said compartments to form an ending narcotics count of narcotics in each of said compartments of said portable cart after the cart has moved among a plurality of patients; and (d) a bar code reader means having an optically sensitive element responding to a bar code identification on medications from said cart.

7. A medication cart for dispensing narcotics to a plurality of patients during nurse rounds, the cart comprising:

(a) a portable cart having N compartments for narcotics stored in said compartments;

(b) lock means for securing said compartments having narcotics therein;

(c) counter means for counting doses of narcotics in each of said N compartments, said counter means having input means thereto for receiving an entry representing the initial doses of narcotics in each of said compartments, said counter means decrementing the beginning narcotics count as doses of narcotics are removed from individual said compartments to form an ending narcotics count of narcotics in each of said compartments of said portable cart after the cart has moved among a plurality of patients; and (d) a card reader on said cart connected with a computer for limiting opening of said lock means to personnel having permissible card indicia as read by said card reader.

8. The apparatus of claim 7 including keyboard means for operator input of a personal identification number assigned to particular personnel for opening said lock means.

9. A medication cart for dispensing narcotics to a plurality of patients during nurse rounds, the cart comprising:

(a) a portable cart having N compartments for narcotics stored in said compartments;

(b) lock means for securing said compartments having narcotics therein;

(c) counter means for counting doses of narcotics in each of said N compartments, said counter means having input means thereto for receiving an entry representing the initial doses of narcotics in each of said compartments, said counter means decrementing the beginning narcotics count as doses of narcotics are removed from individual compartments to form an ending narcotics count of narcotics in each of said compartments of said portable cart after the cart has moved among a plurality of patients and said counter means comprises a CPU and memory on said cart wherein said CPU and memory are provided with personnel identification number inputs to operate said counter means to identify operator personnel.

10. The apparatus of claim 9 including a card reader for badge reading and a keyboard for data entry.

11. The apparatus of claim 9 including means for electronically forming patient records including medicine and narcotic dosage.

* * * * *